United States Patent
Hillebrand

(10) Patent No.: US 8,029,991 B2
(45) Date of Patent: Oct. 4, 2011

(54) METHOD AND FORMULATION FOR THE EXTRACTION OF NUCLEIC ACIDS FROM ANY COMPLEX STARTING MATERIALS

(75) Inventor: Timo Hillebrand, Hoenow (DE)

(73) Assignee: AJ Innuscreen GmbH, Berlin (DE)

( * ) Notice: Subject to any disclaimer, the term of this patent is extended or adjusted under 35 U.S.C. 154(b) by 246 days.

(21) Appl. No.: 12/059,303

(22) Filed: Mar. 31, 2008

(65) Prior Publication Data

US 2009/0011469 A1 Jan. 8, 2009

Related U.S. Application Data

(63) Continuation of application No. PCT/EP2006/066883, filed on Sep. 29, 2006.

(30) Foreign Application Priority Data

Sep. 29, 2005 (DE) .......................... 10 2005 047 736

(51) Int. Cl.
*C12Q 1/68* (2006.01)
*C07H 21/00* (2006.01)

(52) U.S. Cl. .......................................... 435/6; 536/25.4

(58) Field of Classification Search ....... 435/6; 536/25.4
See application file for complete search history.

(56) References Cited

U.S. PATENT DOCUMENTS

| | | | | |
|---|---|---|---|---|
| 5,173,418 A * | 12/1992 | Molin et al. | | 435/198 |
| 5,234,809 A * | 8/1993 | Boom et al. | | 435/91.2 |
| 5,234,824 A * | 8/1993 | Mullis | | 435/91.1 |
| 5,252,474 A * | 10/1993 | Gewain et al. | | 435/91.1 |
| 5,438,127 A * | 8/1995 | Woodard et al. | | 536/25.4 |
| 5,470,740 A * | 11/1995 | Longo et al. | | 435/252.33 |
| 5,523,392 A * | 6/1996 | Woodard et al. | | 536/25.4 |
| 5,561,064 A * | 10/1996 | Marquet et al. | | 435/320.1 |
| 5,606,046 A * | 2/1997 | Woodard et al. | | 536/25.4 |
| 5,610,291 A * | 3/1997 | Woodard et al. | | 536/25.4 |
| 5,616,701 A * | 4/1997 | Woodard et al. | | 536/25.4 |
| 5,650,506 A * | 7/1997 | Woodard et al. | | 536/25.4 |
| 5,674,997 A * | 10/1997 | Woodard et al. | | 536/25.4 |
| 5,861,293 A * | 1/1999 | Kojiri et al. | | 435/193 |
| 5,976,800 A * | 11/1999 | Lau et al. | | 435/6 |
| 5,977,337 A * | 11/1999 | Loosmore et al. | | 536/23.7 |
| 6,027,883 A * | 2/2000 | Herrnstadt et al. | | 435/6 |
| 6,037,465 A * | 3/2000 | Hillebrand et al. | | 536/25.42 |
| 6,218,531 B1 * | 4/2001 | Ekenberg | | 536/25.41 |
| 2001/0018513 A1 * | 8/2001 | Baker | | 536/25.41 |
| 2001/0034435 A1 * | 10/2001 | Nochumson et al. | | 536/23.1 |
| 2001/0041332 A1 * | 11/2001 | Hillebrand et al. | | 435/6 |
| 2002/0001812 A1 * | 1/2002 | Smith et al. | | 435/6 |
| 2002/0042506 A1 * | 4/2002 | Kristyanne et al. | | 536/25.4 |
| 2003/0003455 A1 * | 1/2003 | Rundell et al. | | 435/6 |
| 2003/0215818 A1 * | 11/2003 | Lorenz | | 435/6 |
| 2004/0039188 A1 * | 2/2004 | Gautsch et al. | | 536/24.3 |
| 2004/0091875 A1 * | 5/2004 | Weber et al. | | 435/6 |
| 2005/0019769 A1 * | 1/2005 | Lenz | | 435/6 |
| 2006/0078923 A1 * | 4/2006 | McKernan et al. | | 435/6 |
| 2006/0166331 A1 * | 7/2006 | Au-Yeung et al. | | 435/91.1 |
| 2009/0011469 A1 * | 1/2009 | Timo | | 435/91.1 |

FOREIGN PATENT DOCUMENTS

| | | |
|---|---|---|
| DE | 102 53 351 | 5/2004 |
| EP | 0 512 767 | 5/1992 |
| WO | WO 00/34463 | 6/2000 |
| WO | WO 01/10554 | 2/2001 |
| WO | WO 02/04620 | 1/2002 |

OTHER PUBLICATIONS

Erik H. Willis, et al., "Prep-A-Gene: A Superior Matrix for the Purification of DNA and DNA Fragments", Product Application Focus, Bio-Rad Laboratories, IMMUNO and Becton Dickenson Research Center, vol. 9, No. 1/1990, pp. 92-99.

* cited by examiner

*Primary Examiner* — Ethan C Whisenant
(74) *Attorney, Agent, or Firm* — Oblon, Spivak, McClelland, Maier & Neustadt, L.L.P.

(57) ABSTRACT

The invention relates to a universal and greatly simplified method as well as a composition for isolating nucleic acids from different starting materials containing nucleic acids. The composition contains at least one buffer solution for proteolytically solubilizing biological samples, the buffer containing no chaotropic or antichaotropic component, at least one alcoholic component and/or a detergent, a solid phase, and a wash and elution buffer.

17 Claims, No Drawings

METHOD AND FORMULATION FOR THE EXTRACTION OF NUCLEIC ACIDS FROM ANY COMPLEX STARTING MATERIALS

BACKGROUND OF THE INVENTION

1. Field of the Invention

The invention relates to a universal and greatly simplified method as well as a formulation for isolating a nucleic acid from a variety of starting materials containing nucleic acids which both results a very high quality and high yields of the isolated nucleic acid.

2. Discussion of the Background

Under conventional conditions the isolation of DNA from cells and tissues is carried out such that the starting materials containing the nucleic acids are digested under highly denaturing and reducing conditions, in part with the use of protein-degrading enzymes. The released nucleic acid fraction is purified in phenol/chloroform extraction stages and the nucleic acids are isolated by dialysis or ethanol precipitation from the aqueous phase (Sambrook, J., Fritsch, E. F. und Maniatis, T., 1989, CSH, "Molecular Cloning").

These conventional methods for the isolation of nucleic acids from cells and especially from tissues are very time consuming (in part longer than 48 h), require considerable apparative expenditure and moreover are not realizable under field conditions. In addition, such methods are hazardous to health and environment due to the chemicals used in amounts that are not inconsiderable, such as phenol and chloroform.

Different alternative methods for the isolation of nucleic acids from various biological starting materials allow the elaborate and health-damaging phenol/chloroform extraction of nucleic acids to be circumvented and a reduction in time expenditure to be achieved.

All of these methods are based on a method for the preparative and analytical purification of DNA fragments from agarose gels developed and described for the first time by Vogelstein and Gillespie (Proc. Natl. Acad. Sci. USA, 1979, 76, 615-619). The method combines the dissociation in a saturated solution of a chaotropic salt (NaI) of the agarose containing the bands of the DNA to be isolated with binding of the DNA to glass particles. The DNA fixed to the glass particles is then washed with a wash solution (20 mM Tris HCl [pH 7.2]; 200 mM NaCl; 2 mM EDTA; 50% v/v ethanol) and then separated from the support particles.

Until now, this method has undergone a series of modifications and is currently used for different methods for the extraction and purification of nucleic acids from various sources (Marko, M. A., Chipperfield, R. und Birnboim, H. G., 1982, Anal. Biochem., 121, 382 387).

In addition, a plurality of reagent systems exists worldwide today, predominantly for the purification of DNA fragments from agarose gels and for the isolation of plasmid DNA from bacterial lysates, and also for the isolation of longer chain nucleic acids (genomic DNA, cellular total RNA) from blood, tissues or cell cultures.

All these commercially available kits are based on the well-known principle of binding nucleic acids to mineral supports in the presence of solutions of different chaotropic salts and use suspensions of finely-milled glass powder (e.g. Glasmilk, BIO 101, La Jolla, Calif.), diatomaceous earths (Sigma) or silica gels (Diagen, DE 41 39 664 A1) as support material.

A method for the isolation of nucleic acids practicable for a number of different applications proposed in U.S. Pat. No. 5,234,809. A method is described therein for the isolation of nucleic acids from starting materials containing nucleic acids, whereby the starting material is incubated with a chaotropic buffer and a DNA-binding solid phase. The chaotropic buffer carries out both the lysis of the starting material as well as the binding of the nucleic acids to the solid phase. The method is well suited for the isolation of nucleic acids from small amounts of sample and finds practical use particularly in the area of the isolation of viral nucleic acids.

Specific modifications of these methods concern the use of novel support materials which have applicative advantages for particular problems (WO-A 95/34569).

More recent patent applications disclose that so-called antichaotropic salts can be used very efficiently and successfully as components of lysis/binding buffer systems for the adsorption of nucleic acids to silicate materials known and used by the person skilled in the art (EP 1 135 479 A). The advantage of this method is that by circumvention of the use of chaotropic salts a clearly lower hazard to health is posed by the extraction system. However, a draw-back is that high salt concentrations (>1.5 M) are required in the lysis buffer for an efficient isolation of nucleic acids from a complex biological sample especially with respect to a highest possible nucleic acid recovery. Thus, EP 1 135 479 A discloses that the lysis buffers used contain salt concentrations of between 1.5 M-3 M.

A method is described in the unexamined application DE 43 21 904 A in which an efficient isolation of nucleic acids is possible with a combination of chaotropic high salt buffers and alcoholic components. The lysis buffers disclosed in DE 43 21 904 A always contain salt concentrations of 4 M-8 M, guanidine hydrochloride, guanidine thiocyanate or potassium iodide in particular are used as salts. It is known that these salts bring about lysis of the starting material as well as potent inactivation of nucleolytic enzymes. The addition of an alcohol is carried out after lysis of the starting material. The patent document discloses that the addition of the alcoholic component to the high salt lysis buffer mediates a highly efficient binding of the nucleic acids to the silicate filter material employed. The disadvantage of the use of lysis buffers with high ion strength chaotropic salts is always the restricted and also inefficient use of additional proteolytic enzymes for an effective digestion of complex biological samples, for these enzymes are themselves damaged by the protein-denaturing action of chaotropic buffers. Furthermore, extensive wash stages are needed subsequently to remove the high salt concentrations from the adsorption material employed. It is known to the person skilled in the art that chaotropic salts exert a high inhibitory action on a number of down-stream applications.

A further possibility for the isolation of nucleic acids is disclosed in utility patent application DE 20 20 7793 U. The method includes the binding of nucleic acids to clay minerals in the presence of a salt of a polyvalent cation. The method is considered to be based on the formation of a so-called cation bridge between the nucleic acids to be isolated and the clay minerals. The desorption of the nucleic acids to be isolated does not take place with water or a low salt buffer as with other known methods but with an elution agent which is at least one complexing agent that is specific for the polyvalent cation in the binding buffer. The disadvantage of the invention is in particular that the complexing components (EDTA; EGTA etc.) as part of the elution buffer often greatly inhibit a number of downstream applications. Although the method for the purification of nucleic acids as described in the utility patent specification ought to be feasible without the use of chaotropic salts, a series of buffers of the embodiment examples always contain chaotropic salts (e.g. guanidine salts). This concerns all embodiment examples that describe the isolation of nucleic acids from complex biological samples. It thus appears that the isolation of nucleic acids from complex samples cannot be realized in the absence of chaotropic salts.

DE 198 56 064 A1, DE 102 53 351 A1, DE 699 08 795 T2 and EP 0 796 327 B1 also belong to the background art. Methods for the isolation of nucleic acids are described therein whereby, however, no antichaotropic components are used.

The analysis of the background art illustrates quite impressively that a plurality of possibilities exists for the binding nucleic acids to solid support materials, in particular silicon-based mineral support materials, then to wash and to release once more the nucleic acids from the support material. It is also clear that a plurality of lysis buffer systems can be employed for the isolation of nucleic acids from complex biological samples. The lysis buffer systems described also always contain salt components that are essential for the necessary binding of the nucleic acids to be isolated to the respective preferred support material, whereby the chaotropic salts selected for the binding of the nucleic acids also at the same time carry out the lysis of the starting material. The salt concentrations of the lysis buffers employed always lie in the high-salt range. This also applies to the utility patent specification DE 20 20 7793 U, although as explicitly described there the binding of the nucleic acids with the use of polyvalent cations and the utilization of clay minerals should take place with low concentrations of polyvalent salts. The concentrations of the guanidinium salts used in this utility patent specification for the isolation are the high salt concentrations known to the person skilled in the art.

DETAILED DESCRIPTION OF THE INVENTION

Thus, it was an object of the present invention to eliminate the disadvantages of the solutions described in the background art.

According to the present invention, the above and other objects were achieved by a method and by a formulation for the isolation and purification of a nucleic acid from complex samples which is universally employable, independent of the nature of the starting material, and which can be carried out in the lysis buffer without the high salt concentrations always required hitherto in the background art for binding nucleic acids to support materials.

The method according to the present invention comprises:
1. The digestion of the sample is carried out in previously known buffers without chaotropic or antichaotropic components.
2. The lysis assay is treated subsequently with an alcohol or with a (preferably) nonionic detergent or a mixture of an alcohol and a nonionic detergent and then this mixture is then brought into contact with a nucleic acid-binding solid phase.
3. The solid phase in then optionally washed with previously known wash buffers.
4. The bound nucleic acid is released from the solid phase with a low-salt buffer or with water.

Surprisingly, the inventors of the present invention have found that after lysis of the starting material, the combination of previously known buffers for the proteolytic lysis of biological samples (tissues, whole blood) comprising, for example, SDS, Tris HCl and EDTA, with an alcoholic component or a detergent facilitates the binding of a sample nucleic acid to a mineral glass fiber filter material. The nucleic acid bound to the filter material can be washed with previously known wash buffers, subsequently briefly dried and released once more from the glass fiber material after the addition of water or 10 mM Tris HCl.

The detergent is not particularly limited. Nonionic detergents are preferred. Detergents such as Tween-20; Tween-80; Triton X-100 etc. (optionally high concentration of at least 10 vol. %) or a mixture of detergent/alcohol (also again high concentration of detergent) can be used as nonionic detergent. The detergent can be used in an amount of from 5 to 50 vol. %, preferably 10-40 vol. %, more preferably 10-20 vol. %. If a salt of a polyvalent cation is added, it may be possible to use a lower amount of detergent compared to the amount used if no salt of a polyvalent cation is added.

The low-salt buffer used can be a known wash buffer, an known elution buffer, a buffer that acts as wash and elution buffer and combination of a wash buffer and an elution buffer. A known low-salt buffer is for example a 10 mM Tris HCl.

This means that, contrary to the previously described mechanisms and methodological solution approaches, adsorption of nucleic acids to known mineral support materials can also be carried out in principle without salts. In this way it is possible to carry out the lysis of complex biological samples with a simple and above all universally employable lysis buffer without the previously required high salt components.

If larger amounts of starting materials are used for the isolation of nucleic acids it then becomes clear, however, that the purity of the isolated nucleic acids, measured as ratio 260:280, is often inadequate with the combination of the described lysis buffer and an alcoholic binding buffer component.

Surprisingly, however, a significant increase in the purity of the isolated nucleic acids can be achieved if the alcoholic component is treated with a salt of a polyvalent, preferably divalent, cation. The salt concentrations necessary for this purpose are, however, not in the high salt range as is known to the person skilled in the art from the background art and which has always been described previously. In one embodiment, salts of any polyvalent cation, for example, $Mg^{2+}$, $Al^{3+}$ or both, can be used as long as they do not form a chaotropic or antichaotropic salt. The salts of the polyvalent cation preferably form a non-chaotropic salt, preferably one which is in the middle of the Hoffmeister salt series. Magnesium chloride is preferably used since $MgCl_2$ is neither chaotropic not anti-chaotropic. The amount of the salt of the polyvalent cation is preferably 0.1 M to 1.5 M, including all values and subvalues therebetween.

Chaotropic components are defined as substances that destroy regular structures of liquid water based on the formation of hydrogen bonds in that they inhibit the formation of $H_2O$ cage structures necessary for solvation. Examples of chaotropic components are thiocyanates, iodides or perchlorates. They bring about denaturation of proteins, the increase in the solubility of nonpolar substances in water as well as the destruction of the hydrophobic interaction.

Antichaotropic components are defined as substances that enhance regular structures of liquid water based on the formation of hydrogen bonds. Examples of antichaotropic components are ammonium, sodium or potassium salts. They do not bring about denaturation, but enhance hydrophobic forces and the increase in hydrophobic interactions.

Alcoholic components within the meaning of the present invention are all water-soluble alcohols such as methanol, ethanol, propanol, isopropanol, ethylene glycol, polyethylene glycol or glycerine. The alcohol can be used in an amount of from 20 vol % to 80 vol. %, preferably about 50 vol. %, including all values and subvalues.

The method according to the present invention, based on the combination of a lysis buffer without salts that would conventionally be necessary for the binding of the nucleic acids to a support material with a binding buffer based on an alcoholic component and a salt component of a divalent cation allows the isolation of nucleic acids of high quality from any starting material. Moreover, owing to the low salt concentration use the method can reduce the previously required wash steps, which brings about a clear reduction in so-called "hands on time".

The method is highly efficient and moreover shows that in comparison with the methods and kits hitherto employed world-wide the yields of isolated nucleic acids are at least equivalent. If a detergent component is also added to the binding buffer this combination brings about a yet further increase in the yield of nucleic acids to be isolated. In a preferred embodiment the yield is quantitative. The yield is preferably >90%, more preferably >95%, even more preferably >98%, even more preferably >99% and most preferably 100%. The addition of a detergent in the binding buffer also brings about a significant reduction in the nonspecific adsorption of hemoglobin onto the glass fiber material employed when nucleic acids are to be isolated, for example, from whole blood. This effect also has a positive effect on the extraction process since it is known that multiple washing steps are required to remove hemoglobin from support materials, particularly in methods for the isolation of nucleic acids from whole blood.

Since the lysis buffers used in the method according to the invention contain no components that allow adsorption of nucleic acids it is also possible to carry out, for example, preliminary filtration processes through the same filter material that is also finally used for the adsorption of the nucleic acids. This represents a considerable technological simplification. Thus, for example after lysis of a plant sample the lysate can be centrifuged through a glass fiber filter matrix as part of a centrifugation column to remove unlysed plant materials and inhibitory components. The filtrate is then treated with a binding buffer and transferred to a further centrifuge column with glass fiber matrix. The nucleic acids bind to the fibers of the glass fiber matrix, are washed with an alcohol-containing wash buffer and the bound nucleic acids are then finally eluted from the glass fiber matrix by the addition of, for example, water.

This is equally valid for complex biological samples such as faecal samples or also, i.a., whole blood. Such a simplification cannot be carried out with the previously known systems and methods, which also contain the salt components necessary for the adsorption of the nucleic acids in the lysis buffer.

The method according to the invention, surprisingly, shows a further quite significant new effect. It is known that the support materials employed for the isolation and purification (in combination with the known high salt buffers and optionally alcohols) are glass, ceramics, quartz, silica gels, aerosils, diatomaceous earths, etc. These materials can be porous and non-porous. They can be, for example, components of centrifugation units (centrifugation filter columns) etc. as suspensions or also as fibers, gels, wools or mats. It is known to the person skilled in the art that the binding of polyanions such as, for example, DNA can take place to negative functional surfaces. This basic knowledge represents the scientific background for the use of negative or potentially negative solid phases for the binding of nucleic acids with the known high salt buffers.

Surprisingly, the combination of a lysis buffer for the digestion of the biological sample with the subsequent addition of a binding buffer comprising an alcohol, a salt of a divalent cation and a detergent described in the method according to the invention shows that an efficient binding of nucleic acids makes no specific demands on the support materials used. In addition to the possibility of the use of previously known support materials (in particular with negative functional charges), physically/chemically quite different support material could be used for the isolation and purification of nucleic acids. Named here as examples: positively charged nylon membranes, polysulphone membranes, polyethersulphone membranes, PVDF membranes, membranes from acrylic polymers, ion exchange membranes, polyethylene frits and even simple filter papers, glass fiber materials (e.g. paper filters). This is also all the more very surprising since a number of the membranes described have chemically inert, neutral surfaces and actually are used in practice for filtrations without having the objective of binding affinities for biomolecules.

Moreover, particles are also suitable for the binding of nucleic acids with the described methods (e.g. functionalized magnetic iron oxide particles, silica particles, etc.).

The binding and the final desorption of the nucleic acids to and from these quite different support materials can take place under the same lysis/binding buffer conditions.

This observation suggests a totally novel mechanism through which the process of isolation and purification of nucleic acids is realized.

It becomes clear, however, that the practicability of using different support materials will facilitate quite new product developments in the area of the isolation and purification of nucleic acids. The appropriate combination of lysis/binding buffer with specific support materials offers henceforth the possibility of totally new solution approaches for the isolation of nucleic acids. This is all the more interesting, since methods of molecular sample preparation within the context of rapidly developing molecular diagnostics are in principle becoming increasingly more essential in all aspects of our life.

In the present invention % refers to % by weight for solid components, vol. % for liquid components.

Having generally described this invention, a further understanding can be obtained by reference to certain specific examples which are provided herein for purposes of illustration only, and are not intended to be limiting unless otherwise specified.

EXAMPLES

Example 1

Isolation of Genomic DNA from Tissue Samples using Different Solid Support Materials Each of ca. 5 mg tissue material (pig liver) were incubated with continuous shaking for 30 min at 50° C. in 400 μl lysis buffer (SDS; Tris HCl, pH 8.0, EDTA) in a 1.5 ml reaction vessel with the addition of 25 μl proteinase K (20 mg/ml). After lysis of the starting material the lysis assay was centrifuged at full speed for 1 min to remove unlysed components. The supernatant was then treated with 400 μl binding buffer (50% isopropanol, 10% Tween 20, 0.5 M $MgCl_2$) and mixed. The assay was then transferred to commercially available centrifugation filters provided with different membranes and centrifuged through the membranes. The following membranes were used:
1. glass fiber membranes (Filtrak)
2. tissue quartz (Pall)

3. ion exchange membrane (cation exchanger; Pall)
4. polysulphone membrane (uncharged; Pall)
5. acrylic polymer membrane (uncharged; Pall)
6. filter paper (13 µm; Roth).

The filtrate was then rejected and the centrifuge column washed once with 800 µl wash buffer
(50 mM NaCl; 10 mM Tris HCl; 1 mM EDTA; 70% v/v ethanol).

After the removal of the ethanol in a brief centrifugation step (12,000 rpm for 2 min) the nucleic acids were eluted by the addition of 200 µl an elution buffer (10 mM Tris-HCl; pH 8.5) by centrifugation for
1 min at 10,000 rpm.

Next spectrophotometric measurement of the DNA was carried out.

The results are shown in the following table. In each case 3 extractions were carried out and the measurement values calculated after measurement.

| Membrane | Yield | Ratio 260:280 |
|---|---|---|
| Glass fiber membrane (Filtrak) | 23 µg | 1.92 |
| Tissue quartz (Pall) | 22 µg | 1.77 |
| Ion exchange membrane (cation exchanger; Pall) | 14 µg | 1.97 |
| Polysulphone membrane (uncharged; Pall) | 17 µg | 2.00 |
| Acrylic polymer membrane (uncharged; Pall) | 20 µg | 1.87 |
| Filter paper (13 µm; Roth) | 11 µg | 1.94 |

The results demonstrate that the isolation of nucleic acids can be carried out very efficiently and with high purity with different support materials, and not only the previously used classical silicate materials are suitable. The results also show that a high purity of the nucleic acids is achieved with only one wash step.

Example 2

Each batch of ca. 50 mg liver tissue (mouse) was treated with 400 µl lyse buffer free of chaotropic und antichaotropic components comprising 1% SDS; 10 mM EDTA and 50 mM Tris HCl and 25 µl proteinase K and lysed at 50° C.

After lysis 400 µl of an alcohol/detergent mixture (50 vol. % isopropanol/40 vol. % Tween-20) were added as binding buffer. Lysis assay and binding buffer were mixed thoroughly with a pipette.

The sample was transferred to a centrifuge column with glass fiber filter material and centrifugation at 10,000×g for 1 min. The filtrate was rejected.

Subsequently, the sample was washed twice with ethanolic wash buffer (70 vol. % ethanol, sodium chloride; Tris HCl).

The column was dried by centrifugation for 2 min at 10,000×g.

The DNA was eluted by addition of 200 µl of an elution buffer (10 mM Tris HCl); followed by centrifugation at 5,000×g for 1 min.

Next, the isolated DNA was measured spectrophotometrically.

| Result | | |
|---|---|---|
| Sample | Ratio A260:A280 | Total yield of DNA |
| 1 | 1.87 | 77 µg |
| 2 | 1.84 | 74 µg |
| 3 | 1.86 | 73 µg |
| 4 | 1.88 | 78 µg |
| 5 | 1.83 | 72 µg |

CONCLUSION

The method demonstrates clearly that it is possible to isolate quantitative amounts of nucleic acids by using a mineral support material, glass fiber, known to a person skilled in the art without any use of so-called chaotropic or nonchaotropic salts. All the extraction methods known to the person skilled in the art which bind nucleic acids to a mineral solid phase require the said salts.

German patent application DE 10 2005 047 736.4 filed Sep. 29, 2005 and PCT application PCT/EP2006/066883, filed Sep. 29, 2006, as well as the patents and publications mentioned herein, are incorporated herein by reference in their entirety.

Numerous modifications and variations on the present invention are possible in light of the above teachings. It is therefore to be understood that within the scope of the appended claims, the invention may be practiced otherwise than as specifically described herein.

The invention claimed is:

1. A method for the isolation of a nucleic acid from a starting material containing a nucleic acid, comprising:
    digesting the starting material with a lysis buffer which contains neither a chaotropic nor an antichaotropic component, to obtain a digested component containing said nucleic acid;
    optionally, preliminarily filtering said digested component containing said nucleic acid;
    adding of a member selected from the group consisting of (i) an alcohol, (ii) a detergent and (iii) a mixture of an alcohol and a detergent;
    binding the nucleic acid to a solid phase, to obtain a bound nucleic acid;
    washing the bound nucleic acid with a wash buffer;
    eluting of the bound nucleic acid with a wash buffer, an elution buffer, a combination thereof, or with water, to obtain said nucleic acid;
    wherein said alcohol is added and wherein said alcohol is water-soluble;
    wherein said alcohol comprises at least one salt of a polyvalent cation.

2. The method according to claim 1, wherein said mixture of said alcohol and said detergent are added,
    wherein a fraction of the alcohol in the mixture of alcohol and detergent is 20 to 80 vol. %.

3. The method according to claim 1, wherein said lysis buffer comprises SDS, Tris HCl, EDTA or mixtures thereof.

4. The method according to claim 1, wherein said solid phase is a glass fiber material.

5. The method according to claim 1, wherein said solid phase is selected from the group consisting of a negative functional surface, a positively charged nylon membrane, a polysulphone membrane, a polyethersulphone membrane, a PVDF membrane, a membrane from an acrylic polymer, an ion exchange membrane, a polyethylene frit, a filter paper, a glass fiber material, magnetic iron oxide particles, silicate particles and combinations thereof.

6. The method according to claim 1, wherein said preliminary filtration is performed and wherein the same filter material is used for the preliminary filtration and the binding of the nucleic acid.

7. The method according to claim 1, wherein said alcohol is added and said alcohol is a water-soluble alcohol selected from the group consisting of methanol, ethanol, propanol, isopropanol, ethylene glycol, polyethylene glycol, glycerine and mixtures thereof.

8. The method according to claim 1, wherein said mixture of alcohol and detergent,
wherein a fraction of the alcohol in the mixture of alcohol and detergent is 45 to 55 vol. %.

9. The method according to claim 1, wherein said detergent is added and said detergent is a non-ionic detergent.

10. The method according to claim 1, wherein said filtering is performed.

11. The method according to claim 1, wherein said alcohol comprises at least one salt of a doubly positively charged cation.

12. The method according to claim 1, wherein said alcohol comprises a salt of $Mg^{2+}$, $Al^{3+}$ or both.

13. A composition, comprising:
at least one lysis buffer for the proteolytic digestion of a biological sample which contains no chaotropic or antichaotropic components;
a member selected from the group consisting of (i) an alcohol, (ii) a detergent and (iii) a mixture of an alcohol and a detergent; wherein said alcohol is present and wherein said alcohol is water-soluble;
at least one solid phase; and
a wash buffer, an elution buffer or a combination thereof;
wherein said composition is suitable for the isolation of a nucleic acid from a material containing a nucleic acid; and
wherein said alcohol comprises at least one salt with a polyvalent cation.

14. A composition, comprising:
at least one lysis buffer for the proteolytic digestion of a biological sample which contains no chaotropic or antichaotropic components;
a member selected from the group consisting of (i) an alcohol, (ii) a detergent and (iii) a mixture of an alcohol and a detergent; wherein said alcohol is present and wherein said alcohol is water-soluble;
at least one solid phase; and
a wash buffer, an elution buffer or a combination thereof;
wherein said composition is suitable for the isolation of a nucleic acid from a material containing a nucleic acid; and
wherein said alcohol comprises at least one salt of a doubly positively charged cation.

15. A composition, comprising:
at least one lysis buffer for the proteolytic digestion of a biological sample which contains no chaotropic or antichaotropic components;
a member selected from the group consisting of (i) an alcohol, (ii) a detergent and (iii) a mixture of an alcohol and a detergent; wherein said alcohol is present and wherein said alcohol is water-soluble;
at least one solid phase; and
a wash buffer, an elution buffer or a combination thereof;
wherein said composition is suitable for the isolation of a nucleic acid from a material containing a nucleic acid; and
wherein said alcohol comprises a salt of $Mg^{2+}$, $Al^{3+}$ or both.

16. The composition according to claim 13, wherein a concentration of the salt of the polyvalent cation does not exceed 1.5 mol/l.

17. A method of using a buffer for the proteolytic digestion of a biological sample, comprising:
contacting said buffer which comprises no chaotropic or antichaotropic component with a material containing a nucleic acid and isolating said nucleic acid;
wherein a member selected from the group consisting of (i) an alcohol, (ii) a detergent and (iii) a mixture of an alcohol and a detergent is added;
wherein said alcohol is added and wherein said alcohol is water-soluble; and
wherein said alcohol comprises at least one salt of a polyvalent cation.

* * * * *